US009157882B2

(12) United States Patent
Moffat et al.

(10) Patent No.: US 9,157,882 B2
(45) Date of Patent: Oct. 13, 2015

(54) ANALYTICAL TEST STRIP

(71) Applicant: LifeScan Scotland Limited, Inverness, Inverness-shire (GB)

(72) Inventors: James T. Moffat, Inverness (GB); Lawrence Ritchie, Inverness (GB); Steven John Setford, Ross-shire (GB); John Scott, Inverness (GB); Graeme J. Webster, Inverness (GB)

(73) Assignee: Cilag GmbH International, Zug (CH)

( * ) Notice: Subject to any disclaimer, the term of this patent is extended or adjusted under 35 U.S.C. 154(b) by 105 days.

(21) Appl. No.: 13/722,869

(22) Filed: Dec. 20, 2012

(65) Prior Publication Data

US 2014/0174947 A1    Jun. 26, 2014

(51) Int. Cl.
*C12Q 1/00* (2006.01)
*G01N 27/327* (2006.01)

(52) U.S. Cl.
CPC ................................. *G01N 27/3272* (2013.01)

(58) Field of Classification Search
CPC ... G01N 27/3272; G01N 33/64; G01N 33/66; G01N 2333/904; C12Q 1/006; C12Q 1/54
See application file for complete search history.

(56) References Cited

U.S. PATENT DOCUMENTS

| 6,942,518 | B2 | 9/2005 | Liamos et al. |
| 7,914,335 | B2 | 3/2011 | Stafford et al. |
| 8,066,858 | B2 | 11/2011 | Wang et al. |
| 8,083,993 | B2 | 12/2011 | Groll |
| 2009/0029479 | A1 | 1/2009 | Docherty et al. |
| 2012/0305396 | A1* | 12/2012 | Harding et al. .......... 204/403.14 |
| 2012/0312699 | A1* | 12/2012 | Webster et al. ............... 205/792 |

FOREIGN PATENT DOCUMENTS

| EP | 1 382 968 A1 | 1/2004 |
| WO | WO 2011/094315 A1 | 8/2011 |

* cited by examiner

*Primary Examiner* — Gurpreet Kaur

(57) ABSTRACT

An analytical test strip has mutually-insulated first and second electrodes arranged to define a sample-receiving chamber. Electrically-insulating layers are disposed over respective electrodes. First and second electrical contact pads are electrically connected to the first electrode, and a third pad to the second electrode. A first side of the test strip has a first electrically-insulating layer and the third pad, and a second side has the second electrically-insulating layer and the first and second pads. The third pad extends longitudinally from the sample-receiving chamber farther than does the first electrically-insulating layer. Methods for determining an analyte in a bodily-fluid sample and analytical test systems for use in the determination of an analyte in a bodily-fluid sample are also described.

7 Claims, 6 Drawing Sheets

ANALYTICAL TEST STRIP

CROSS-REFERENCE TO RELATED APPLICATIONS

Reference is made to commonly-assigned U.S. application Ser. Nos. 13/154,875 and 13/250,779, each of which is incorporated herein by reference in their entirety.

TECHNICAL FIELD

The present application relates generally to medical devices, and particularly to analytical test strips, combinations of the same with test meters, and related methods.

BACKGROUND

The determination (e.g., detection or concentration measurement) of an analyte in a fluid sample is of particular interest in the medical field. For example, it can be desirable to determine glucose, ketone bodies, cholesterol, lipoproteins, triglycerides, acetaminophen or HbA1c concentrations in a sample of a bodily fluid such as urine, blood, plasma or interstitial fluid. Such determinations can be achieved using an analytical test strip and test meter combination.

BRIEF DESCRIPTION OF THE INVENTION

According to an aspect, there is provided an analytical test strip having a first side and an opposing second side, said test strip being defined by a longitudinal axis and a lateral axis, the analytical test strip comprising:
   a) a first electrode and a second electrode electrically insulated from said first electrode, wherein said first and second electrodes are arranged to define a sample-receiving chamber;
   b) a first electrically-insulating layer disposed over said first electrode, and a second electrically-insulating layer disposed over said second electrode;
   c) a first electrical contact pad and a second electrical contact pad electrically connected to the first electrical contact pad, the first and second electrical contact pads electrically connected to the first electrode; and
   d) a third electrical contact pad electrically connected to the second electrode;
   wherein the first side comprises the first electrically-insulating layer and the third electrical contact pad, and the second side comprises the second electrically-insulating layer and the first and second electrical contact pads; and
   wherein the third electrical contact pad extends longitudinally from the sample-receiving chamber farther than does the first electrically-insulating layer.

According to another aspect, there is provided a method for determining an analyte in a bodily-fluid sample, the method comprising:
   receiving an analytical test strip inserted in a longitudinal direction into a test-strip-receiving module of a test meter so that first and second electrical contact pads exposed on a second side of the analytical test strip make electrical contact with first and second electrical connector pins of the test-strip-receiving module, respectively, and a third electrical contact pad exposed on a first side of the analytical test strip makes electrical contact with a third electrical connector pin of the test-strip receiving module, the analytical test strip including a sample-receiving chamber adapted to receive a bodily-fluid sample;
   wherein the third electrical contact pad is arranged laterally between the first and second electrical contact pads of the analytical test strip, and
   wherein the third electrical contact pad is disposed such that said third electrical pad extends longitudinally from the sample-receiving chamber by a distance greater than either the first electrical contact pad or the second electrical contact pad;
   sensing, using a signal processing module of the test meter, electrical continuity between the first electrical connector pin of the test-strip-receiving module and the second electrical connector pin of the test strip receiving module via the first electrical contact pad and the second electrical contact pad of the analytical test strip;
   when continuity is sensed, the signal processing module automatically applying a selected electrical signal to the third electrical connector pin and either the first or the second electrical connector pin and measuring a resulting electrical signal; and
   the signal processing module automatically processing the resulting electrical signal to detect whether a bodily-fluid sample has been applied to the sample-receiving chamber and, if so, the signal-processing module automatically determining the analyte in the applied bodily-fluid sample using the resulting electrical signal.

According to another aspect, there is provided an analytical test system for use in the determination of an analyte in a bodily-fluid sample, the analytical test system comprising:
   a) a test meter with:
      i) a test-strip-receiving module with first, second, and third electrical connector pins; and
      ii) a signal processing module; and
   b) an analytical test strip with lateral and longitudinal axes, the test strip having:
      i) first and second electrodes;
      ii) first and second electrical contact pads electrically connected to the first electrode, each pad configured to communicate an electrical response of the first electrode to the test meter should the test meter be in electrical communication with that pad;
      iii) a third electrical contact pad protruding longitudinally beyond the first and second electrical contact pads and electrically connected to the second electrode, the third electrical contact pad being configured to communicate an electrical response of the second electrode to the test meter should the test meter be in electrical communication with the third electrical contact pad;
      iv) in which the test-strip-receiving module is arranged such that the first, second, and third electrical connector pins make electrical connection with the first, second, and third electrical contact pads, respectively, when the analytical test strip is inserted into the test-strip receiving module; and
   wherein the signal processing module is configured to:
      i) detect the test strip by sensing electrical continuity between the first and second electrical connector pins;
      ii) apply a selected electrical signal to the third electrical pin and either the first or the second electrical connector pin after the test strip is detected and measure a result electrical signal; and
      iii) process the result electrical signal to detect the bodily-fluid sample and, if the bodily-fluid sample is present, determine the analyte.

Various aspects advantageously provide detection of a test strip and determination of an analyte. Various aspects advantageously permit simple connectors to be used to connect to test strips.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

The attached drawings are for purposes of illustration and are not necessarily to scale, in each dimension individually or in any set of dimensions together.

DETAILED DESCRIPTION OF THE INVENTION

The following description relates to exemplary embodiments of an analytical test strip as well as use thereof in determining at least one analyte from a bodily fluid sample. In order to provide a suitable frame of reference with regard to the accompanying drawings, certain terms are used throughout. These terms are not intended to narrow the scope of the concepts detailed herein, including those embodied in the claims unless specifically indicated. In addition and in the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems or methods described herein. Other aspects of such algorithms and systems, and hardware or software for producing and otherwise processing the signals involved therewith, not specifically shown or described herein, are selected from such systems, algorithms, components, and elements known in the art. Given the systems or methods as described herein, software not specifically shown, suggested, or described herein that is useful for implementation of any aspect is conventional and within the ordinary skill in such arts.

Throughout this disclosure, any discussion of a feature being between two other features in a particular direction does not require that feature be on a straight line between the two other features. For example, the stem of a capital Y is between the upper-left and upper-right diagonal segments of the Y in a horizontal direction, even though the stem is below any straight line between those segments.

Figure 1:
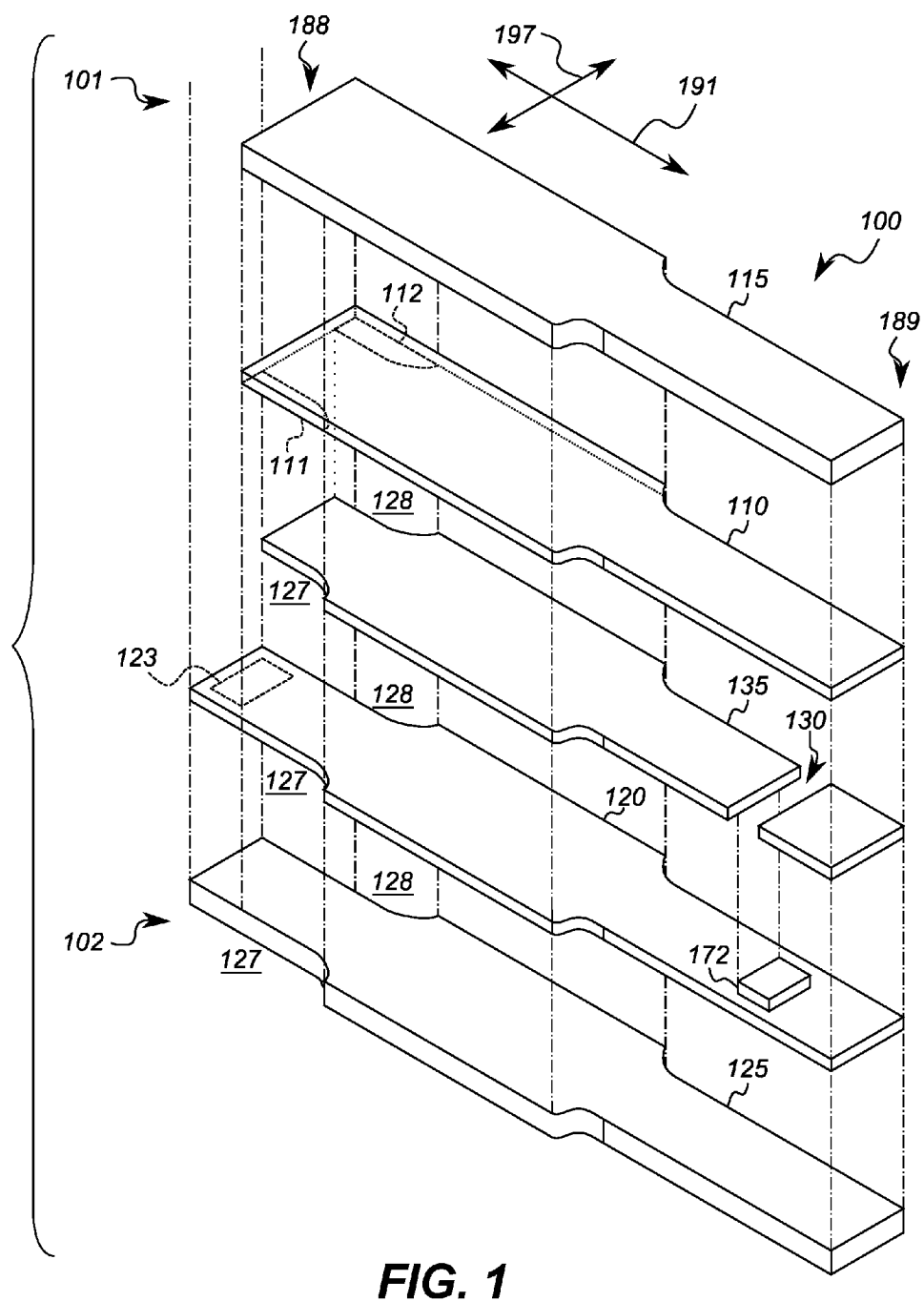
FIG. 1 is an axonometric exploded top view of an exemplary test strip.

FIG. 1 is an axonometric exploded top view of an exemplary test strip. As noted above and throughout this disclosure, the terms "top" and "bottom" are used for clarity and do not constrain the orientation of the herein described test strip.

More specifically and according to this embodiment, the test strip 100 can be defined by a first or top side 101 and an opposing second or bottom side 102, and opposed ends 188, 189. Moreover, the test strip 100 can be further defined by a primary longitudinal axis 191 and a smaller lateral axis 197, as indicated according to FIG. 1. As shown, the axes 191, 197 are not parallel to one another; that is, these axes intersect one another and can be disposed at any convenient angle. According to one version, the axes can be orthogonal or can be situated at another convenient angle, e.g., 90°±10° or 45°.

Figure 2:
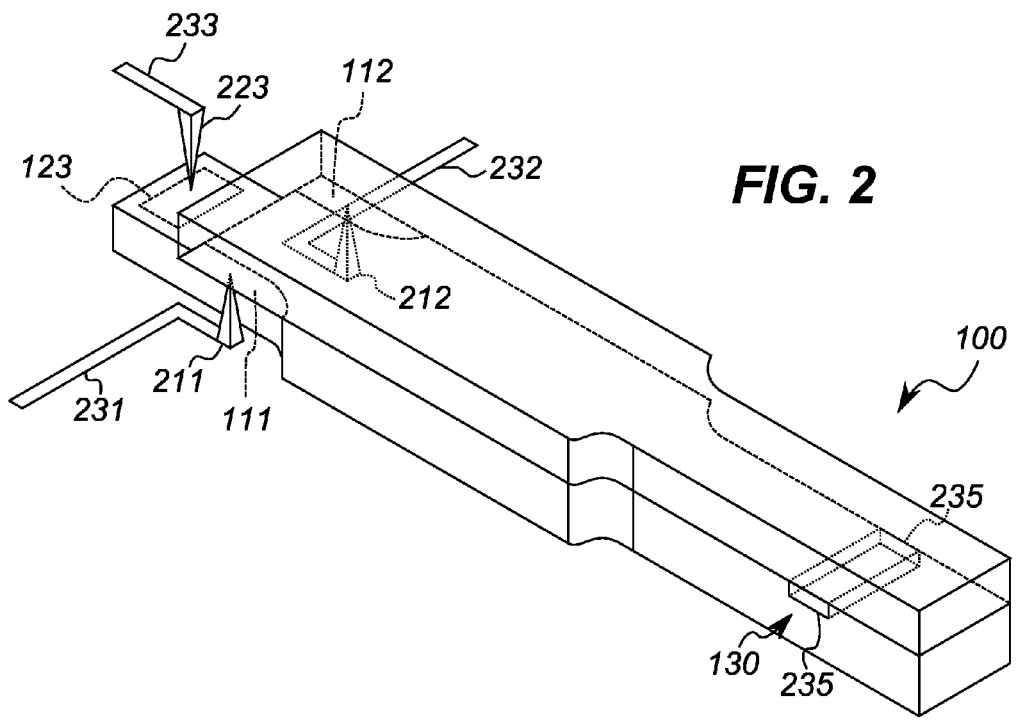
FIG. 2 is an perspective view of the test strip of FIG. 1.
Figure 3:
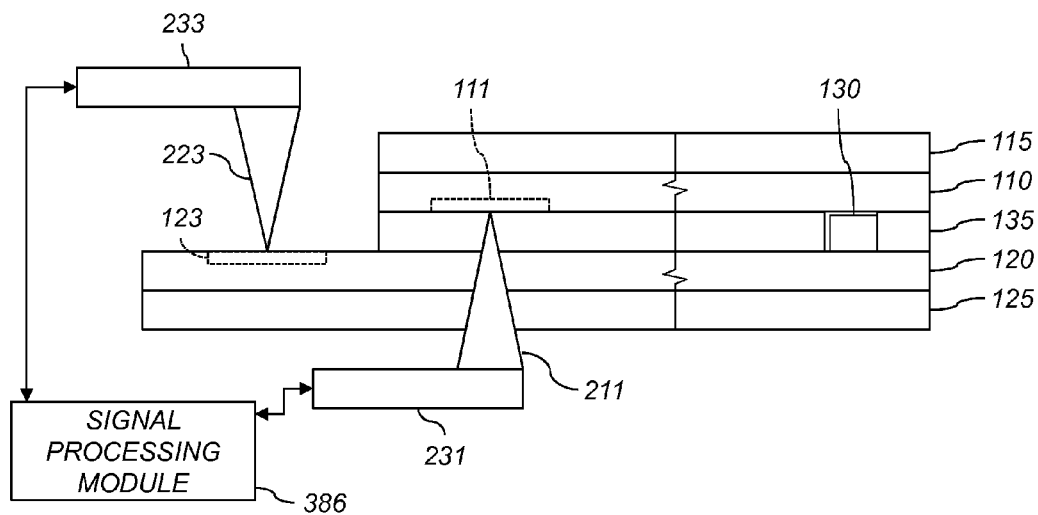
FIG. 3 is a side partially diagrammatic view of the test strip of FIGS. 1 and 2, as inserted into an electrical connector according to various aspects.

In terms of the construction of the test strip, a first electrode 110 and a second electrode 120 are arranged to define a sample-receiving chamber 130, shown more clearly in FIGS. 2 and 3. The second electrode 120 is electrically insulated from the first electrode 110 in a sandwiched format. In one version, the first electrode 110 includes gold (Au) and electrode 120 includes palladium (Pd).

A first electrically-insulating layer 115, e.g., a top insulator, is disposed over the first electrode 110 and can cover the whole surface or only a portion thereof. A second electrically-insulating layer 125, e.g., a bottom insulator, is disposed beneath the second electrode 120 and can also cover the whole surface or a portion thereof.

The electrodes, e.g., electrodes 110, 120, can be thin films. In various aspects, electrodes include conductive material formed from materials such as gold, palladium, carbon, silver, platinum, tin oxide, iridium, indium, and combinations thereof (e.g., indium-doped tin oxide or "ITO"). Electrodes can be formed by disposing a conductive material onto electrically-insulating layers 125, 115 by a sputtering, electroless plating, or a screen printing process. In an example, sputtered gold electrode 110 is disposed over the side not visible in FIG. 1 of electrically-insulating layer 115, and sputtered palladium electrode 120 is disposed over the side visible in FIG. 1 of electrically-insulating layer 125. Suitable materials that can be employed as electrically-insulating layers include, for example, plastics (e.g. PET, PETG, polyimide, polycarbonate, polystyrene), silicon, ceramic, glass, and combinations thereof. For example, first and second insulating layers 115, 125 can be formed from 7 mil polyester substrate(s).

According to this exemplary embodiment, at least one electrically-insulating spacer 135 can be arranged between the first electrode 110 and the second electrode 120. As shown in FIGS. 1-3, a sample-receiving chamber 130 can be formed by removing a portion of the spacer 135, or by disposing two separated portions of the spacer 135 between the first and second electrodes 110, 120.

Still referring to FIG. 1, a first electrical contact pad 111 and a second electrical contact pad 112 are electrically connected to the first electrode 110. In this embodiment, each of the contact pads 111, 112 are applied on the underside of the first electrode 110 wherein the second electrical contact pad 112 is electrically connected to the first electrical contact pad 111. A third electrical contact pad 123 is electrically connected to the second electrode 120 and according to the depicted version, is applied to a top surface thereof. In various aspects, the contact pads 111, 112, 123 are disposed apart from the first and second electrodes 110, 120 and are in electrical communication therewith. In other aspects, such as depicted according to FIG. 1, the first and second electrodes 110, 120 extend to encompass the pads 111, 112, 123, such that the contact pads 111, 112, 123 are defined areas of electrodes 110, 120.

The first or top side of the herein described test strip 100 comprises the first electrically-insulating layer 115 and third electrical contact pad 123. In general, first side 101 includes components visible when looking down on test strip 100 from above. The second or bottom side 102 comprises the second electrically-insulating layer 125 as well as the first and second electrical contact pads 111, 112 applied to the underside of the first electrode 110. This arrangement is discussed below with reference to FIG. 3. Details of various exemplary test strips and measurement methods are provided in US Patent Application Publication No. 2007/0074977, incorporated herein by reference.

As more clearly shown in FIGS. 2 and 3 and according to this embodiment, the third electrical contact pad 123, the supporting second electrically-insulating layer 120 and the bottom insulating layer 127 each extend outwardly in a longitudinal direction along axis 191 from the remainder of the test strip 100, which includes the first electrode 110 including the first and second contact pads 111, 112, the top insulating layer 115 and the spacer 135. The extending portions of the test strip 100 are provided at the end 188 and oppositely from the end 189 of the test strip adjacent the defined sample receiving chamber 130. This configuration provides access to the third contact pad 123 from the first side 101 of the test strip 100 and access to the first and second contact pads from the second side 102.

Therefore and in this test strip configuration, the third electrical contact pad 123 extends longitudinally farther from the sample-receiving chamber 130 than either of the first and second electrical contact pads 111, 112. Moreover and according to the depicted design and as shown in FIG. 2, the third electrical contact pad 123 is disposed laterally between the first and second electrical contact pads 111, 112.

Referring back to FIG. 1, in this exemplary configuration each of the second electrically-insulating layer 125 and the second electrode 120 includes corresponding first and second cutout portions 127, 128 provided at the end 188 of the test strip 100 and are configured and sized to expose corresponding the first electrode 110 and more specifically the first and second electrical contact pads 111, 112. According to the present embodiment, the cutout portions 127, 128 in the bottom insulating layer 125 are aligned with the cutout portions 127, 128 formed in the second electrode 120. In various aspects, the first and second cutout portions 127, 128 are disposed on opposing lateral sides of test strip 100. Spacer 130 can also include cutout portions 127, 128, as can other layers between first electrode 110 and second insulating layer 125, or on layers the opposite of second insulating layer 125 from first electrode 110. As shown by the widely-spaced-dotted line, the corner of the cutout portion 128 in spacer 130 aligns with the laterally-interior corner of the contact pad 112 at end 188 of the test strip 100.

In various aspects, test strip 100 can be readily and inexpensively manufactured using a web-based punching process. Individual layers or combinations of the sandwiched layers can be punched from a web to form components of test strip 100, and the resulting components can be stacked and bonded to form the test strip 100. Electrically-insulating layers 115, 125, or spacer 60, can be sufficiently rigid to provide mechanical support to test strip 100, or can be layers coated or otherwise disposed over other sufficiently rigid structures.

In various aspects, sample-receiving chamber 130 is adapted for analyzing small volume samples. For example, sample-receiving chamber 130 can have a volume ranging from about 0.1 microliters to about 5 microliters, or 0.2 to about 3 microliters, or about 0.3 microliters to about 1 microliter. To accommodate a small sample volume, the electrodes 110 and 120 can be closely spaced. For example, where the spacer 135 defines the distance between the second electrode 120 and the first electrode 110, the height of spacer 135 can be in the range of about 1 micron to about 500 microns, or between about 10 microns and about 400 microns, or between about 40 microns and about 200 microns. More details of exemplary test strips are given in U.S. Pat. No. 8,163,162, incorporated herein by reference.

One or more electrical conductors can be disposed over each of the top and bottom electrically-insulating layers 115, 125. In the example shown, the second electrode 120 can be disposed over the electrically-insulating layer 125 adjacent to sample-receiving chamber 130. Electrodes 110, 120 can be arranged spaced apart in a facing or opposing faced arrangement, or in other coplanar or non-coplanar configurations.

A reagent layer 172 can be disposed within the sample-receiving chamber 130 using a process such as slot coating, coating by dispensing liquid from the end of a tube, ink jetting, and screen printing. Such processes are described, for example, in the following U.S. Pat. Nos. 6,749,887; 6,689, 411; 6,676, 995; and 6,830,934, each of which is incorporated by reference herein. In various aspects, the reagent layer 172 is deposited onto an electrode (in the example shown, electrode 120) and includes at least a mediator and an enzyme. A mediator can be in either of two redox states which may be referred to as an oxidizable substance or a reducible substance. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on a pyrroloquinoline quinone co-factor, and GDH based on a nicotinamide adenine dinucleotide co-factor. One exemplary reagent formulation for reagent layer 172 is described in U.S. application Ser. No. 10/242,951, entitled, Method for Manufacturing a Sterilized and Calibrated Biosensor-Based Medical Device, published as U.S. Patent Application Publication No. 2004/0120848, which is hereby incorporated by reference in its entirety.

In an example, support layer 125 includes a polyester base on which has been deposited, e.g., by sputtering, a Pd coating forming working electrode 120. Dry reagent layer 172 includes buffer, mediator, and enzyme, as described herein. Spacer 135 is a double-sided adhesive having a cutout area that defines the electrochemical cell (sample-receiving chamber 130). Spacer 135 can be less than about 200 um thick. Electrically-insulating layer 115 includes a polyester base on which has been deposited, e.g., by sputtering, an Au coating forming reference electrode 110. In this example, a glucose oxidase/ferricyanide system is used to determine glucose concentrations via the following reactions:

glucose+glucose oxidase→gluconic acid+reduced glucose oxidase     Reaction 1 reduced glucose oxidase+2ferricyanide→glucose oxi-
dase+2ferrocyanide.  Reaction 2

Ferricyanide ($[Fe(CN)_6]^{3-}$) is the mediator, which returns the reduced glucose oxidase to its catalytic state. Glucose oxidase, an enzyme catalyst, will continue to oxidize glucose so long as excess mediator is present. Ferrocyanide ($[Fe(CN)_6]^{4-}$) is the product of the total reaction. Ideally, there is no ferrocyanide initially, although in practice there is often a small quantity. After the reaction is complete, the concentration of ferrocyanide (measured electrochemically) indicates the initial concentration of glucose. The total reaction is the sum of reactions 1 and 2.

glucose+2ferricyanide→gluconic acid+2ferrocyanide  Reaction 3

"Glucose" refers specifically to β-D-glucose. Details of this system are described in PCT Application No. WO 97/18465 and U.S. Pat. No. 6,444,115, each of which is incorporated herein by reference.

FIG. 2 is an axonometric view of the exemplary test strip 100. First, second, and third electrical connector pins 211, 212, 233, respectively, are provided as part of a test-strip receiving module 386 (FIG. 3). The electrical connector pins 211, 212, 233 make electrical connection with the first, second, and third electrical contact pads 111, 112, 123, respectively, when the test strip 100 is inserted into the test-strip receiving module. Conductors 231, 232, 233 carry signals to and from pins 211, 212, 213, respectively. Pins 211, 212, 233 can be pogo pins, spring fingers, or other connector types. It should be noted that the pyramidal shape of the pins shown is exemplary.

Sample-receiving chamber 130 includes an aperture 235 arranged so that a fluid sample, e.g., a whole blood sample, brought into contact with aperture 235, i.e., into contact with the edges or sidewalls of sample-receiving chamber 130, is drawn into sample-receiving chamber 130, e.g., by capillary action. Sample-receiving chamber 130 can have more than one aperture 235; in the example shown, chamber 130 has two laterally-opposed apertures 235. One of the apertures 235 can provide a sample inlet and the other aperture 235 can act as a vent. In various aspects, the bodily-fluid sample is a whole blood sample and the analyte is glucose.

FIG. 3 is a side view of the test strip 100, as inserted into an electrical connector according to one version. As shown in each of FIGS. 2 and 3, each of the electrical connector pins 211, 212, and 223 can be compliant or movable, or mounted on compliant or movable supports. Conductors 231, 232, and 233 are electrically connected to a signal processing module 386, as described below.

Figure 4:
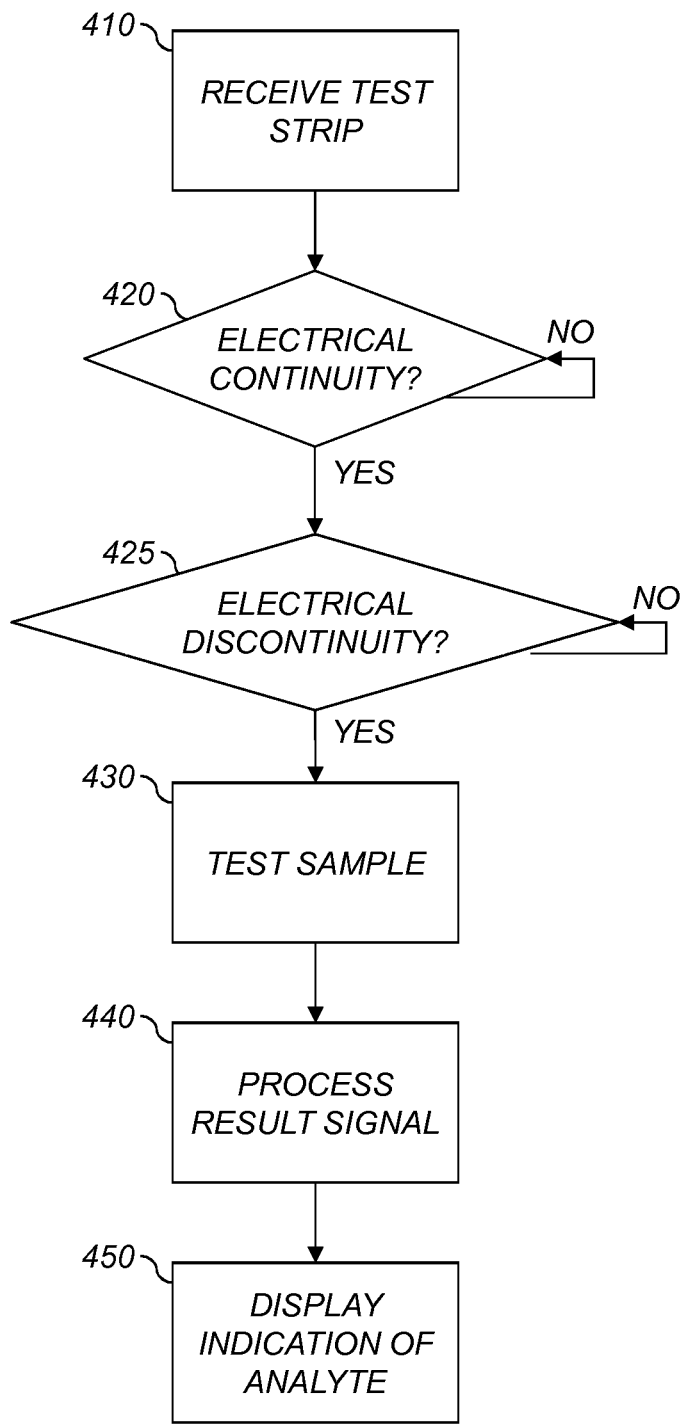
FIG. 4 is a flowchart detailing an exemplary method for determining an analyte in a bodily-fluid sample using a test strip.

FIG. 4 is a flowchart of ways of determining an analyte in a bodily-fluid sample according to various embodiments. Processing begins with step 410.

In step 410, an analytical test strip inserted in a longitudinal direction into a test-strip-receiving module of a test meter is received. The analytical test strip including a sample-receiving chamber adapted to receive a bodily-fluid sample, and first, second, and third electrical contact pads. As a result of or as part of the receiving step and according to the exemplary version, the first and second electrical contact pads (e.g., Au pads) exposed on a second side of the analytical test strip make electrical contact with first and second electrical connector pins of the test-strip-receiving module, respectively. A third electrical contact pad exposed on a first side of the analytical test strip makes electrical contact with a third electrical connector pin (e.g., Pd pads) of the test-strip receiving module. The third electrical contact pad is arranged laterally between the first and second electrical contact pads of the analytical test strip. The third electrical contact pad is further disposed in accordance with this exemplary embodiment so that the third contact pad longitudinally extends at the far end of the test strip from the sample-receiving chamber by a distance greater than either the first electrical contact pad or the second electrical contact pad does. Step 410 is followed by step 420.

In an example, the analytical test strip is test strip 100 shown in FIG. 2. The test-strip-receiving module includes pins 211, 212, 223, which make contact with electrical contact pads 111, 112, 123, respectively.

In step 420, a signal processing module of the test meter is used to sense electrical continuity between the first electrical connector pin of the test-strip-receiving module and the second electrical connector pin of the test strip receiving module via the first electrical contact pad and the second electrical contact pad of the analytical test strip. For purposes discussed herein the signal processing module can include or be part of the signal processing module 386 (FIG. 3). When continuity is sensed, step 420 is followed by step 430. Otherwise, step 420 can be followed by step 425.

For example, as discussed previously and with reference to FIG. 1, on suitable test strips, the second electrical contact pad 112 is electrically connected to the first electrical contact pad 111. If no continuity is detected, the signal processing module can wait for continuity, prompt a user to insert a strip, or signal an error. Failure to detect continuity can be a result of non-insertion of a test strip, insertion of the test strip less than fully, or insertion of a test strip that does not have electrically-connected pads 111, 112 positioned to make electrical contact with the connector pins 211, 212.

In step 425, which can be part of the sensing step 420, the signal processing module senses electrical discontinuity between the third electrical connector pin and either the first or the second electrical connector pin. Testing step 430 is performed when both continuity between the first and second electrical connector pins and discontinuity between the third electrical connector pin and either the first or the second electrical connector pin are sensed. Steps 420 and 425 are shown sequentially, each waiting for a single condition, but they can be performed simultaneously or in either order.

In step 430, when continuity is sensed, the signal processing module tests the inserted test strip. To do this, the signal processing module automatically applies a selected electrical signal to the third electrical connector pin and either the first or the second electrical connector pin and measures a resulting electrical signal. Step 430 is followed by step 440.

In step 440, the signal processing module automatically processes the measured resulting electrical signal to detect whether a bodily-fluid sample has been applied to the sample-receiving chamber. If a sample has been applied, the signal-processing module automatically determines the analyte in the applied bodily-fluid sample using the resulting electrical signal. In an example, the analyte is glucose and the bodily-fluid sample is a whole blood sample. Step 440 can be followed by step 450.

In step 450, in various aspects, after processing step 440, the signal processing module automatically displaying an indication of the determined analyte. The indication can be presented on a display, e.g., by the signal processing module automatically commanding the display. For example, the level of glucose in a blood sample, measured in mg/dL or mmol/L, can be displayed as a number.

Figure 5:
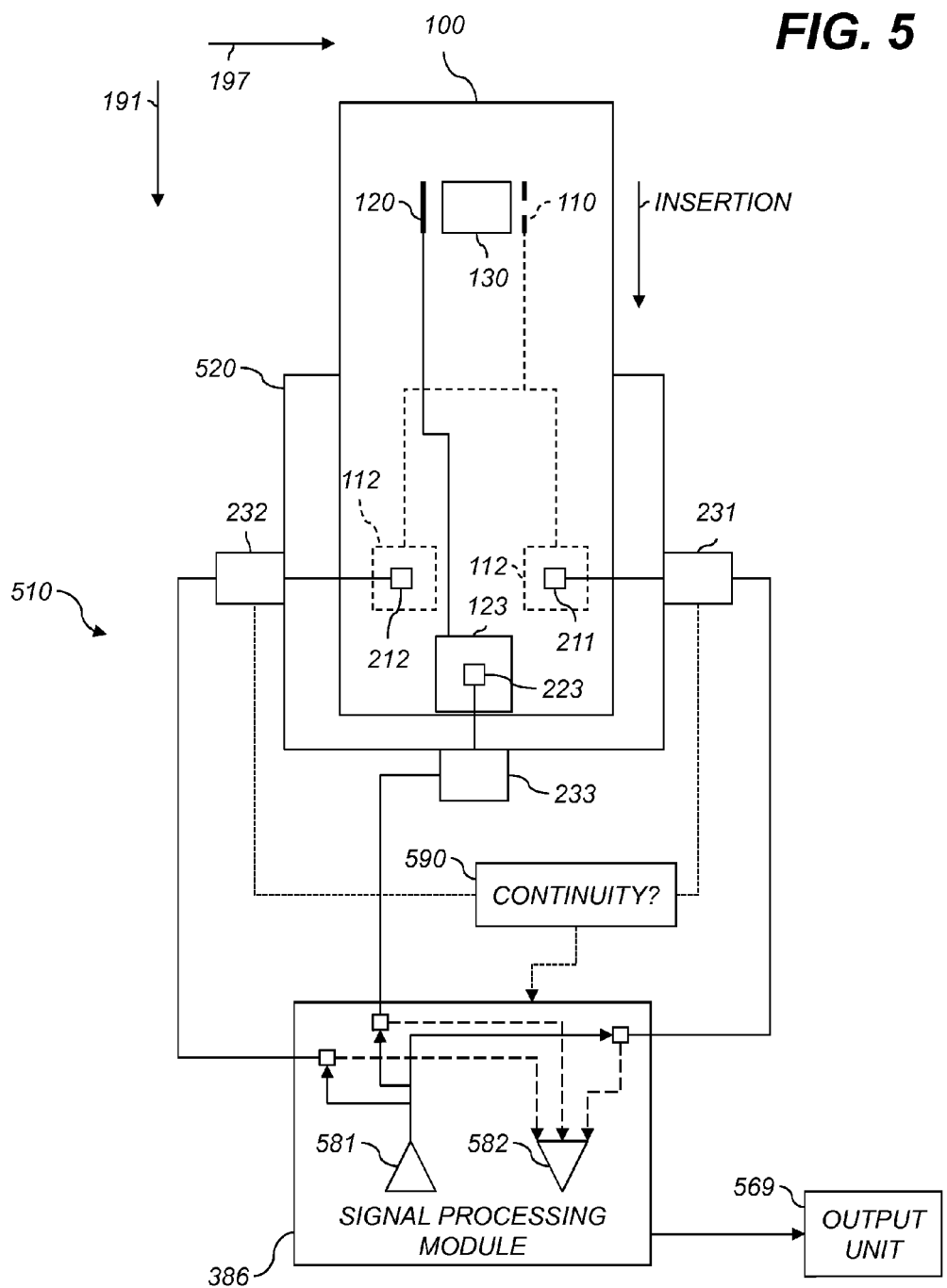
FIG. 5 is an diagrammatic view of a test strip as used in an analytical test system according to various aspects.

FIG. 5 is a schematic representation of components of an analytical test system according to various aspects. A "test set" or "test pairing" is such a system including an analytical test strip 100 and a test meter 510. Test meter 510 is considered an associated test meter with respect to an analytical test strip 100.

The analytical test system is adapted to determine an analyte in a bodily-fluid sample. Test meter 510 includes a test-strip-receiving module 520. Test-strip-receiving module 520 can include electrical or mechanical structures adapted to receive or retain analytical test strip 100. According to the exemplary version, test-strip-receiving module 520 has at least first, second, and third electrical connector pins 211, 212, 223.

The signal processing module 386 controls operation of the system. Signal processing module 386 can include a microcontroller, microprocessor, field-programmable gate array (FPGA), programmable logic array or device (PLA or PLD), programmable array logic (PAL) device, digital signal processor (DSP), or other logic or processing component adapted to perform functions described herein, or more than one of any of those, in any combination.

As previously noted, the analytical test strip 100, FIG. 1, has a lateral axis 197 and a longitudinal axis 191. Test strip 100 has first and second electrodes 110, 120 operatively arranged with respect to the sample-receiving chamber 130. First and second electrical contact pads 111, 112 are electrically connected to the first electrode 110. Each electrical contact pad 111, 112 is configured to communicate an electrical response of the first electrode 110 to the test meter 510 in electrical communication with that pad 111, 112, e.g., by making contact when test strip 100 is inserted in test-strip-receiving module 520. Test strip 100 can include a variety of electrical contact configurations for electrically connecting to test meter 510. For example, U.S. Pat. No. 6,379,513 discloses electrochemical cell connections, and is hereby incorporated by reference in its entirety.

The third electrical contact pad 123 of test strip 100 protrudes longitudinally outwardly beyond either of the first and second electrical contact pads 111, 112. Contact pad 123 is electrically connected to the second electrode 120 and is configured to communicate an electrical response of the second electrode 120 to the test meter 510 when the test meter 510 is in electrical communication with the third electrical contact pad 123. First and second electrical contact pads 111, 112 can be disposed in a predetermined spatial relationship relative to third electrical contact pad 123. Test-strip-receiving module 520 is arranged such that the first, second, and third electrical connector pins 211, 212, 223 make electrical connection with the first, second, and third electrical contact pads 111, 112, 123, respectively, when test strip 100 is inserted into test-strip receiving module 520. Signal processing module 386 or related components are electrically connected to electrodes 231, 232, 233, which are electrically connected to pins 211, 212, 223 respectively.

Signal processing module 386 is configured to detect test strip 100 by sensing electrical continuity between first and second electrical connector pins 211, 212. As discussed above, signal processing module 386 can wait for a strip, prompt for a strip, or take other actions until continuity is detected. Signal processing module 386 can also enter a low-power mode, e.g., a sleep mode, until continuity is detected. Also as discussed above, signal processing module 386 can sense electrical discontinuity between the third electrical connector pin 223 and either the first or the second electrical connector pin 211 to detect test strip 100. This can advantageously reduce the probability of false detection, e.g., if conductive articles (e.g., foil wrappers for sticks of gum) enter test-strip-receiving module and short pins 211, 212, and 223 all together.

In the example shown, signal processing module 386 senses continuity by communicating with continuity sensor 590. Continuity sensor 590 is electrically connected to conductors 231 and 232 and can thus detect an electrical connection between pins 211 and 212. For clarity, these electrical connections are shown dashed. In the example shown, this connection is made when test strip 100 is substantially fully inserted into test-strip-receiving module 520. In various aspects, continuity sensor 590 is wholly or partly a component of signal processing module 386, or is a separate component communicating with signal processing module 386. Continuity sensor 590 can apply a test voltage or current, sense a test current, voltage, or magnetic field, or perform any combination of those.

When continuity is detected, i.e., the test strip is detected to be present, signal processing module 386 applies a selected electrical signal to third electrical pin 223 and either the first or the second electrical connector pin 211, 212 (or both) of the detected test strip using driver 581. Driver 581 can be a voltage source, current source, arbitrary waveform source, or other device adapted to produce electrical signals. Signal processing module then measures a result electrical signal on pin 211, 212, or 223, or any combination thereof, using detector 582. Detector 582 can include an ADC, sample-and-hold, meter, Hall-effect sensor, or other device adapted to measure electrical signals. In an example, a voltage is applied between pins 211 and 223 and the resulting current through those pins is measured. Driver 581 and detector 582 can be connected to conductors 231, 232, 233 through respective couplers 531, 532, 533. Couplers 531, 532, 533 can include pass transistors, RF couplers, gates, or other devices adapted to permit driver 581 to apply signals to electrical conductors 231, 232, 233 and to permit detector 582 to, simultaneously or not, measure electrical properties of conductors 231, 232, 233 or signals carried thereon. Couplers 531, 532, 533 can include electrical shorts, so the output of driver 581 is connected directly to the input of detector 582, and signal processing module 386 or detector 582 can include echo-suppression or echo-cancellation circuitry, logic, or code (not shown) to remove driver 581's output from the received signal. In FIG. 5, couplers 531, 532, 533 are represented graphically as squares. For clarity, connections to detector 582 are shown dashed.

Signal processing module 386 processes the result electrical signal to detect the bodily-fluid sample and, if the bodily-fluid sample is present, determine the analyte. This is discussed below. In various aspects, signal processing module 386 communicates an indication of the determined analyte, or other status information (e.g., "no strip present" or "no sample present") using output unit 569. Output unit 669 can include a light that blinks when controller 686 presents the error, a bell, beeper or buzzer that sounds, a horn that blows, an audio- or visual-reproduction system that activates (e.g., a computer screen that displays a pop-up error dialog), or a network interface that transmits information about the error to a human-machine interface (HMI), server, terminal, smartphone, pager, or other computing or communications device.

Still referring to FIG. 5, an electrochemical (amperometric) method for measuring an analyte concentration in an aqueous sample, e.g., a bodily-fluid sample, involves placing the sample into a reaction zone in an electrochemical cell (e.g., sample-receiving chamber 130) that has two electrodes (e.g., electrodes 110, 120) having an impedance that is suitable for the amperometric measurement. The analyte is allowed to react directly with an electrode or with a redox reagent, as described above, to form an oxidizable (or reducible) substance in an amount that corresponds to the analyte concentration. The quantity of oxidizable (or reducible) substance is then determined electrochemically. Various aspects accurately determine the point in time at which the sample is detected in the reaction zone. This permits an electrochemical waveform (e.g., voltage) to be applied immediately after the sample has been applied and accurately defines an incubation period or reaction time. In turn, this improves the accuracy and precision of the assay.

In various aspects, first, a small, constant current source is applied across the electrode of an electrochemical diagnostic strip and a potential difference between the electrodes is monitored. Before the sample is applied to sample-receiving chamber 130, there is a dry gap between electrodes 110, 120. Therefore, negligible current flows. When a sample is applied to the strip and fills the gap, the measured voltage decreases rapidly, causing the test time to be initiated. Signal processing module 386 recognizes the decrease in voltage as indicative of a sample and automatically stops applying a constant-current electrical signal to the selected pins (e.g., pins 111 and 123 or 112 and 123). The controller then applies a constant-voltage electrical signal to the selected pins. While the constant voltage is applied, current or charge are measured as a function of time to permit the analyte concentration to be calculated.

The current a predetermined time after the constant voltage is applied is a measure of the analyte concentration, once the system has been calibrated using samples having known analyte concentrations. The duration of the predetermined time is not critical. It can be at least about 3 seconds when the fluid is blood and the analyte is glucose. That duration generally provides sufficient time to dissolve reagents and reduce an amount of mediator that is readily measurable. All things being equal, at high hematocrit, longer times are needed. The duration can be <10 seconds. The same predetermined time can be used for multiple successive measurements of respective samples. Further examples are given in U.S. Pat. No. 6,193,873, incorporated herein by reference.

Referring back to FIG. 1, in various aspects, third electrical contact pad 123 is arranged laterally between first and second electrical contact pads 111, 112. In various aspects, test strip 100 has first side 101 and second side 102. First and second electrical connector pins 211, 212 (FIG. 2) are arranged to make electrical contact with first and second electrical contact pads 111, 112 from second side 102 of test strip 100. Third electrical connector pin 223 (FIG. 2) is arranged to make electrical contact with third electrical contact pad 123 from first side 101 of test strip 100.

In various aspects, test strip 100 includes opposed first and second sides 101, 102. Second side 102 includes second electrically-insulating layer 125 disposed over second electrode 120. Each of second electrically-insulating layer 125 and second electrode 120 includes corresponding first and second cutout portions 127, 128. Cutout portions 127, 128 expose corresponding areas of first electrode 110 to define first and second electrical contact pads 111, 112. In various aspects, first and second cutout portions 127, 128 are arranged on opposing lateral sides of test strip 100.

Analytical test strip and test meter combinations according to various aspects are beneficial in that the analytical test strips can be readily identified as suitable or unsuitable for use by the test meter based on whether signal processing module 386 senses an electrical continuity or an electrical discontinuity between pins 211, 212. Such identification advantageously permits the test meter to proceed with analyte determination only when appropriate, thus avoiding potentially improper, erroneous or inaccurate analyte determinations based on the use of unsuitable analytical test strips.

It is envisioned that various commercial markets can be supplied with analytical test strip and meter combinations according to various aspects. For example, commercial market "A" can be supplied with test meters described herein that have pins 211, 212 in a predetermined spatial relationship that results in the sensing of electrical continuity. Commercial market "B" can be supplied with test meters that have pins in a different spatial relationship than that of pins 211, 212 in market A's meters. Therefore, using test strip 100 in a market-B test meter results in the sensing of electrical discontinuity. In such a scenario, signal processing modules of test meters supplied to users in markets A and B would be programmed to identify analyte test strips with the appropriate electrical continuity or discontinuity as suitable for use and analyte test strips with inappropriate electrical continuity or discontinuity as unsuitable for use. If an analytical test meter configured for market B were to be inadvertently employed in market A, a market-A test strip would not have electrical continuity, and the signal-processing module in the market-B test meter would determine that the analytical test strip was unsuitable for use and, if desired, display an appropriate message to a user on a display module of the test meter.

Figure 6:
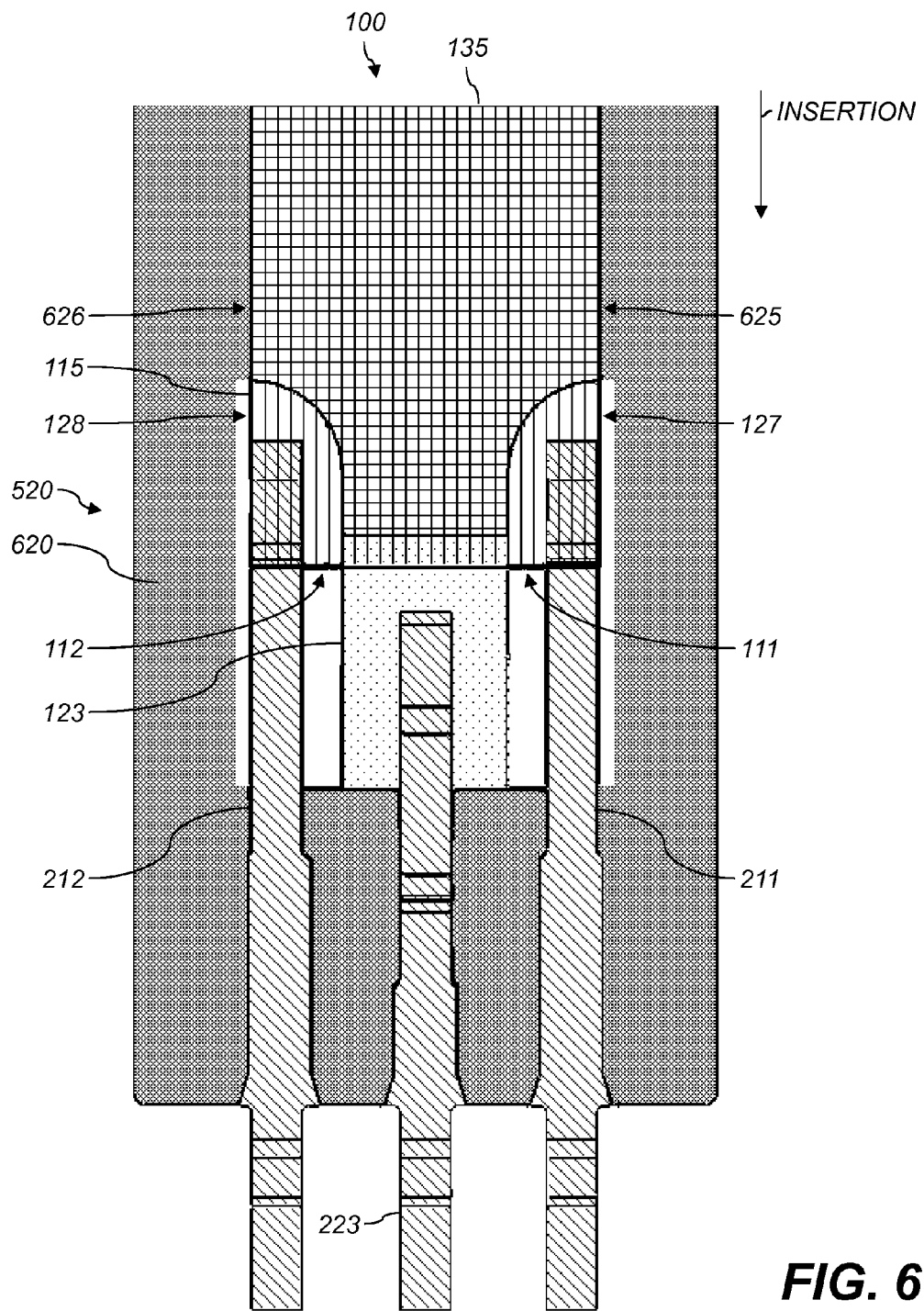
FIG. 6 is a partially-sectioned top view of an exemplary test-strip-receiving module and test strip.

FIG. 6 is a partially-transparent top view of test-strip-receiving module 520, e.g., an electrical connector, and test strip 100 according to various aspects. Test strip 100 has first electrically-insulating layer 115 (hatched with vertical lines), under which is spacer 135 (horizontal lines). Cutout areas 127, 128 (FIG. 1) are the areas hatched only with vertical lines, and define pads 111, 112. Pad 123 (light halftone) is disposed over bottom insulator 125 (FIG. 1). Test-strip-receiving module has a housing 620 (dark halftone), to which are mounted pins 211, 212, 223 (diagonal lines). Pins 211, 212, 223 make contact with pads 111, 112, 123, respectively, when test strip 100 is substantially fully inserted into test-strip-receiving module 520. Sidewalls 625, 626 in housing 620 mechanically guide test strip 100 to promote proper registration between pads 111, 112, 123 and pins 211, 212, 223, respectively. As shown, pins 211, 212 are below first electrically-insulating layer 115, and pin 223 is above pad 123 (mounted on or over second electrically-insulating layer 125 shown in FIG. 1).

Figure 7:
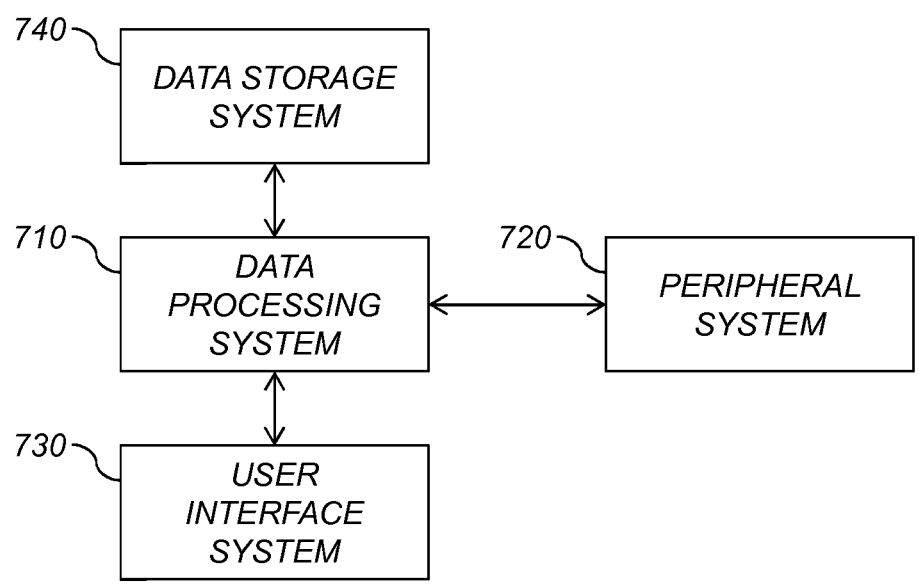
FIG. 7 is a block diagram showing components of a data-processing system.

FIG. 7 is a block diagram showing components of a data-processing system for analyzing data and performing other analyses described herein. The system includes a data processing system 710, a peripheral system 720, a user interface system 730, and a data storage system 740. The peripheral system 720, the user interface system 730 and the data storage system 740 are communicatively connected to the data processing system 710. Signal processing module 386 can include one or more of systems 710, 720, 730, 740.

The data processing system 710 includes one or more data processing devices that implement the processes of the various aspects, including the example processes described herein. The phrases "data processing device" or "data processor" are intended to include any data processing device, such as a central processing unit ("CPU"), a desktop computer, a laptop computer, a mainframe computer, a personal digital assistant, a BLACKBERRY, a digital camera, cellular phone, or any other device for processing data, managing data, or handling data, whether implemented with electrical, magnetic, optical, biological components, or otherwise.

The data storage system 740 includes one or more processor-accessible memories configured to store information, including the information needed to execute the processes of the various aspects, including the example processes described herein. The data storage system 740 can be a distributed processor-accessible memory system including multiple processor-accessible memories communicatively connected to the data processing system 710 via a plurality of computers or devices. On the other hand, the data storage system 740 need not be a distributed processor-accessible memory system and, consequently, can include one or more processor-accessible memories located within a single data processor or device. In various aspects, data storage system 740 in signal processing module 386 (FIG. 5) includes code or other commands to cause signal processing module 386 to carry out a suitable algorithm that determines an analyte based on the electrochemical response of analytical test strip 100 (FIG. 5). The algorithm can accommodate the electrochemical response of electrodes 110, 120 (FIG. 5) within electrochemical-based analytical test strip 100.

The phrase "processor-accessible memory" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMS.

The phrase "communicatively connected" is intended to include any type of connection, whether wired or wireless, between devices, data processors, or programs in which data can be communicated. The phrase "communicatively connected" is intended to include a connection between devices or programs within a single data processor, a connection between devices or programs located in different data processors, and a connection between devices not located in data processors. In this regard, although the data storage system 740 is shown separately from the data processing system 710, one skilled in the art will appreciate that the data storage system 740 can be stored completely or partially within the data processing system 710. Further in this regard, although the peripheral system 720 and the user interface system 730 are shown separately from the data processing system 710, one skilled in the art will appreciate that one or both of such systems can be stored completely or partially within the data processing system 710.

The peripheral system 720 can include one or more devices configured to provide digital content records to the data processing system 710. For example, the peripheral system 720 can include digital still cameras, digital video cameras, cellular phones, or other data processors. The data processing system 710, upon receipt of digital content records from a device in the peripheral system 720, can store such digital content records in the data storage system 740.

The user interface system 730 can include a mouse, a keyboard, another computer, or any device or combination of devices from which data is input to the data processing system 710. In this regard, although the peripheral system 720 is shown separately from the user interface system 730, the peripheral system 720 can be included as part of the user interface system 730.

The user interface system 730 also can include a display device, a processor-accessible memory, or any device or combination of devices to which data is output by the data processing system 710. In this regard, if the user interface system 730 includes a processor-accessible memory, such memory can be part of the data storage system 740 even though the user interface system 730 and the data storage system 740 are shown separately in FIG. 7.

Aspects of the present invention can be embodied as a system, method, or computer program product. Accordingly, aspects may take the form of entirely hardware, entirely software (including firmware, resident software, micro-code, etc.), or a combination of software and hardware. These forms and aspects can all generally be referred to herein as a "service," "circuit," "circuitry," "module," or "system."

Various aspects may take the form of a computer program product embodied in one or more computer readable medium(s) having computer readable program code embodied thereon. A computer program product can include one or more storage media, for example: magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice various aspects. Other examples of computer-readable storage media include a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. A computer readable storage medium may be any tangible medium that can contain, or store a program for use by or in connection with an instruction execution system, apparatus, or device.

Program code or executable instructions embodied on a computer readable medium may be transmitted using any appropriate medium, including but not limited to wireless, wireline, optical fiber cable, RF, or any suitable combination of appropriate media.

Computer program code for carrying out operations for various aspects can execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Computer program instructions can be stored in a computer readable medium that can direct a computer, other programmable data processing apparatus, or other devices to function in a particular manner. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

PARTS LIST FOR FIGS. 1-7

100 test strip
101,102 side
110 electrode
111, 112 electrical contact pad
115 electrically-insulating layer
120 electrode
123 electrical contact pad
125 electrically-insulating layer
127, 128 cutout portion
130 sample-receiving chamber
135 spacer 172 reagent
188, 189 end
191 longitudinal axis
197 lateral axis
211, 212, 223 pin
231, 232, 233 conductor
235 aperture
386 signal processing module
410 receive test strip step
420 electrical continuity detected decision step
425 electrical discontinuity detected decision step
430 test sample step
440 process result signal step
450 display indication step
510 test meter
520 test-strip-receiving module
569 output unit
581 driver
582 detector
590 continuity sensor
620 housing
625, 626 sidewall The invention is inclusive of combinations of the aspects described herein. References to "a particular aspect" and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. An analytical test strip having a first side and an opposing second side, said test strip being defined by a longitudinal axis and a lateral axis, the analytical test strip comprising:
   a) a first electrode and a second electrode electrically insulated from said first electrode, wherein said first and second electrodes are arranged to define a sample-receiving chamber;
   b) a first electrically-insulating layer disposed over said first electrode, and a second electrically-insulating layer disposed over said second electrode;
   c) a first electrical contact pad and a second electrical contact pad electrically connected to the first electrical contact pad, the first and second electrical contact pads electrically connected to the first electrode; and
   d) a third electrical contact pad electrically connected to the second electrode;
   wherein the first side comprises the first electrically-insulating layer and the third electrical contact pad, and the second side comprises the second electrically-insulating layer and the first and second electrical contact pads; and
   wherein the third electrical contact pad extends longitudinally from the sample-receiving chamber farther than does the first electrically-insulating layer, thereby exposing the third electrical contact pad of the second electrode without any cutout portion in the first electrically-insulating layer.

2. The analytical test strip according to claim 1, wherein the third electrical contact pad is disposed laterally between the first and second electrical contact pads.

3. The analytical test strip according to claim 1, wherein each of the second electrically-insulating layer and the second electrode includes corresponding first and second cutout portions, wherein the cutout portions expose corresponding areas of the first electrode defining the first and second electrical contact pads.

4. The analytical test strip according to claim 3, wherein the first and second cutout portions are disposed on opposing lateral sides of the analytical test strip.

5. The analytical test strip according to claim 1, wherein the third electrical contact pad extends longitudinally farther from the sample-receiving chamber than either the first electrical contact pad or the second electrical contact pad.

6. The analytical test strip according to claim 1, wherein the analyte is glucose and the sample-receiving chamber includes an aperture arranged so that a whole blood sample brought into contact with the aperture is drawn into the sample-receiving chamber.

7. The analytical test strip according to claim 1, further including at least one electrically-insulating spacer arranged between the first electrode and the second electrode.

* * * * *